(12) United States Patent
Meegan et al.

(10) Patent No.: US 9,795,514 B2
(45) Date of Patent: *Oct. 24, 2017

(54) HIGH FIDELITY BLAST HEARING PROTECTION

(71) Applicant: Applied Research Associates, Inc., Albuquerque, NM (US)

(72) Inventors: George Douglas Meegan, Littleton, CO (US); Theodore Francis Argo, Lakewood, CO (US); Jennifer Nicole Congdon, Wheat Ridge, CO (US)

(73) Assignee: Applied Research Associates, Inc., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/289,400

(22) Filed: Oct. 10, 2016

(65) Prior Publication Data
US 2017/0035616 A1   Feb. 9, 2017

Related U.S. Application Data

(63) Continuation of application No. 14/340,599, filed on Jul. 25, 2014, now Pat. No. 9,463,118.
(Continued)

(51) Int. Cl.
*A61F 11/06* (2006.01)
*H04R 1/02* (2006.01)
(Continued)

(52) U.S. Cl.
CPC ............ *A61F 11/08* (2013.01); *H04R 1/1083* (2013.01); *A61F 2011/085* (2013.01)

(58) Field of Classification Search
CPC .... A61F 11/06; A61F 11/08; A61F 2011/085; G10K 11/175; H04R 1/1008;
(Continued)

(56) References Cited

U.S. PATENT DOCUMENTS

| 4,441,576 A | * | 4/1984 | Allen ...................... A61F 11/08 |
| | | | 128/867 |
| 4,852,683 A | | 8/1989 | Killion |
| | | | (Continued) |

FOREIGN PATENT DOCUMENTS

| DE | 4217043 A1 | 11/1992 |
| DE | 202004002412 A1 | 9/2004 |
| | (Continued) | |

OTHER PUBLICATIONS

U.S. Appl. No. 61/862,786, filed Aug. 6, 2013, G. Douglas Meegan.
(Continued)

*Primary Examiner* — Khai N Nguyen
(74) *Attorney, Agent, or Firm* — Dinsmore & Shohl LLP; Monika L'Orsa Jaensson, Esq.

(57) ABSTRACT

An improved hearing protection device intended to be inserted into an external auditory meatus of a user, having a housing structure, a passive tuning element, and a passive, nonlinear acoustic filter. The tuning element and the acoustic filter may be supported in series by the housing structure. The tuning element may be or include a diaphragm, a resonator, or both. The housing structure may support a diaphragm of the tuning element at its circumference, and may provide cavities on both sides of the diaphragm. In some embodiments electronic components are included in the hearing protection device to counteract insertion loss provided by the passive element, and restore natural hearing for low to moderate sound pressure levels. Communications devices may also be incorporated into the hearing protection device. The combination of a simple, low cost amplifier circuit, passive tuning element and nonlinear acoustic filter of some embodiments of the present invention achieve a low cost yet sophisticated ability to react to impulse noise without the need for a microprocessor or complex electronics. Furthermore, the configuration reduces power consump-
(Continued)

tion and, therefore, increases service life or decreases battery size/capacity, and results in low electronic self-noise allowing the user to maintain situational awareness.

20 Claims, 11 Drawing Sheets

Related U.S. Application Data

(60) Provisional application No. 61/862,786, filed on Aug. 6, 2013.

(51) Int. Cl.
*A61F 11/08* (2006.01)
*H04R 1/10* (2006.01)

(58) Field of Classification Search
CPC .... H04R 1/1083; H04R 1/1091; H04R 25/65; H04R 25/652; H04R 2460/15
USPC ....... 381/23.1, 71.1, 72, 352, 353, 354, 372, 381/380, 411
See application file for complete search history.

(56) References Cited

U.S. PATENT DOCUMENTS

| | | | |
|---|---|---|---|
| 5,113,967 A * | 5/1992 | Killion | A61F 11/08 181/132 |
| 5,402,493 A | 3/1995 | Goldstein | |
| 5,488,961 A * | 2/1996 | Adams | A61F 11/08 128/864 |
| 6,068,079 A | 5/2000 | Hamery | |
| 6,070,693 A | 6/2000 | Hamery | |
| 6,148,821 A | 11/2000 | Falco | |
| 7,697,706 B2 | 4/2010 | Doty | |
| 8,249,285 B2 | 8/2012 | Killion | |
| 8,550,206 B2 | 10/2013 | Keady | |
| 8,649,540 B2 | 2/2014 | Killion | |
| 2006/0045284 A1 * | 3/2006 | Haussmann | A61F 11/08 381/72 |
| 2006/0177083 A1 * | 8/2006 | Sjursen | H04R 19/016 381/322 |
| 2009/0034775 A1 * | 2/2009 | Burton | H04R 1/1016 381/380 |
| 2010/0040250 A1 * | 2/2010 | Gebert | H04R 25/654 381/316 |
| 2010/0329475 A1 | 12/2010 | Killion | |
| 2011/0103605 A1 | 5/2011 | Killion | |
| 2012/0305329 A1 * | 12/2012 | Keady | H04R 25/656 181/135 |

FOREIGN PATENT DOCUMENTS

| | | |
|---|---|---|
| EP | 0440572 A1 | 7/1991 |
| EP | 0590698 A2 | 6/1994 |
| EP | 0955025 A1 | 10/1999 |
| FR | 2050740 A5 | 4/1971 |
| WO | 2011078659 A1 | 12/2009 |

OTHER PUBLICATIONS

3M, "3M™ Combat Arms™ Single Tip Corded Earplugs 370-1031, Hearing Conservation, Medium-Regular, 50 pr/cs" http://solutions.3m.com/wps/portal/3M/en_US/3M-PPE-Safety-Solutions/Personal-Protective-Equipment/Products/Product-Catalog/~/3M-Combat-Arms-Single-Tip-Corded-Earplugs-370-1030-SMALL-50-EA-Case?N=4606+8690968+3294529207+3294780125&rt=rud, Accessed Jul. 25, 2014.

Johnson, D.I, "3M™ Military Combat Safety Gear, Combat Arms™ Earplugs", Blast Overpressure Studies, U.S. Army Medical Res. and Material, DAMD17-93-C3101, http://multimedia.3m.com/msw/media/851487O/combat-arms-earplugs.pdf, 1998, Accessed Jul. 25, 2014.

* cited by examiner

HIGH FIDELITY BLAST HEARING PROTECTION

This invention was made with government support under USAMRMC Contract No. W81XWH-12-C-0121, awarded by the Telemedicine and Advanced Technology Research Center (TATRC). The government has certain rights to the inventions described in this application.

BACKGROUND OF THE INVENTION

The present invention regards a device for providing hearing protection against continuous and impulsive noise exposure using passive methods. Users of the device will benefit from being able to maintain situational awareness while protecting their hearing from harmful loud noises. In some embodiments the passive methods are paired with active electronic components and/or communications equipment to form what are hereafter referred to as hybrid hearing protectors.

Hearing protection heretofore developed typically includes the use of electronic components and methods for providing blast protection while maintaining situational awareness. For example, high-speed digital electronic processing is employed in electronic hearing protectors to achieve 1) a flat frequency response under quiet conditions, and 2) hearing protection under conditions with loud impulsive noises such as blasts. These devices are typically expensive due to the need for high-speed digital electronic processing.

As an example, U.S. Pat. No. 4,985,925 (Langberg et al., "Active Noise Reduction System") uses a combination of passive attenuators and active electronics for hearing protection. Langberg's method as described relies on a complex use of active electronic noise reduction circuitry, summing microphones and filter/feedback methods, all of which render a relatively expensive device when reduced to practice.

Therefore, there is a need to provide hearing protection against continuous and impulsive noise exposure that avoids the use of expensive components, such as high-speed digital electronic processing and complex circuitry.

GENERAL DESCRIPTION OF THE INVENTION

The hearing protection device of the present invention passively achieves a flat-frequency response by means of a nonlinear acoustic filter and a tuning element (hereafter the combination of the non-linear filter and tuning element will be called the 'passive element'). The passive element of the device of the present invention protects the ear from sudden blasts or impulsive noises. The device has potential use as a low-cost hearing protection device with superior performance as compared to existing passive hearing protection devices. Specifically, the flat frequency response provided by the passive element is similar to the frequency response provided by musician's quality earplugs, without the need for custom ear molds and expensive manufacturing, and the blast protection provided by the passive element of the device of the present invention is superior to most passive hearing protection devices.

Some embodiments of the hearing protection device of the present invention include a combination of the passive element of the device of the present invention in combination with an active electronic element, which counteracts the insertion loss provided by the passive element and restores natural hearing for low to moderate sound pressure levels. The active electronic element comprises generally a microphone, an electronic amplifier circuit, and a speaker, to restore natural hearing.

DETAILED DESCRIPTION OF EMBODIMENTS OF THE INVENTION

As depicted by embodiments shown in the figures, the hearing protection device of the present invention passively achieves a flat-frequency response and blast protection (without electronic processing) by means of a passive element 1 comprising a nonlinear acoustic filter 11 and a tuning element 12, supported in a housing structure 2.

Figure 1:
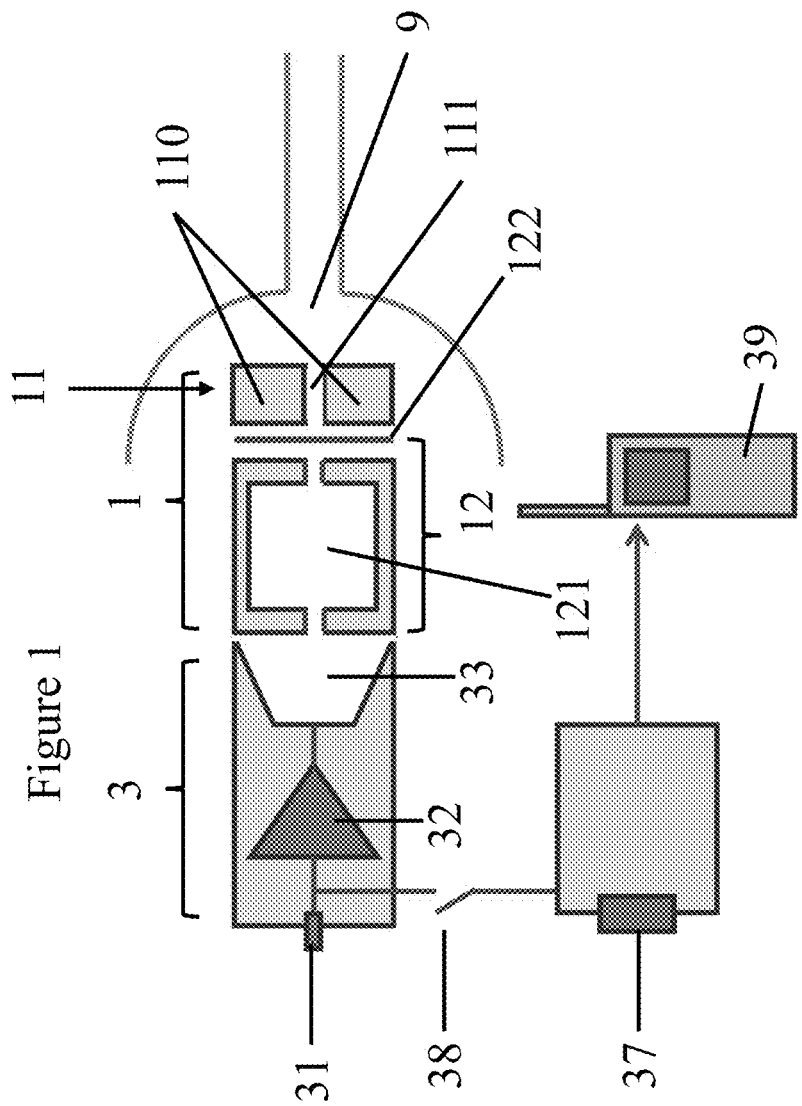
FIG. 1 is a schematic of an embodiment of the present invention.

As shown in FIG. 1, the nonlinear acoustic filter 11 comprises one or more walls 110 (FIG. 1 depicts a single wall), each having one or more small, precision orifice(s) 111. Each wall 110 has a thickness of between 0.005" and 0.200", or between 0.010" and 0.025"; in some embodiments the wall 110 has a thickness of about 0.012". Preferably, the walls are made substantially from acrylonitrile butadiene styrene (ABS) plastic. Alternatively, the walls may be fabricated from any solid material such as plastic or metal. When multiple walls are used, they are layered with spacing between walls ranging from 0.001" and 0.200", or between 0.010" and 0.025". In some embodiments of multiple-walled filters the orifices 111 of the walls 110 may be aligned, however in other embodiments the orifices of the walls are not aligned.

The orifice(s) 111 allow lower-level sounds to pass through the acoustic filter 11 with limited insertion loss while providing increased insertion loss as noise levels increase, thereby resulting in a nonlinear acoustic response which preferentially attenuates loud noises (high sound pressure levels) such as impulsive blasts. The more intense the impulse or noise received by the device, the more it is attenuated by the acoustic filter 11. Specifically, as the amplitude of sound increases, the particle velocity of the oscillatory flow within the orifice increases; as these high particle velocity sound waves pass through the orifice(s) 111, the same are attenuated due to viscous drag and pressure drop across the orifice 111 (viscous drag and pressure drop increase as the particle velocity of the sound waves increase).

For ease of manufacturing, each orifice 111 may be cylindrical in shape. The orifices may have a diameter of between 0.005" and 0.140"; in some embodiments the orifice(s) have a diameter between 0.010" and 0.070"; in some embodiments the orifice(s) have a diameter of about 0.014". In some embodiments (as shown in FIG. 3) the orifice 111 of the passive element 1 is positioned at the end of the ear-tip base 23 described below.

Figure 4:
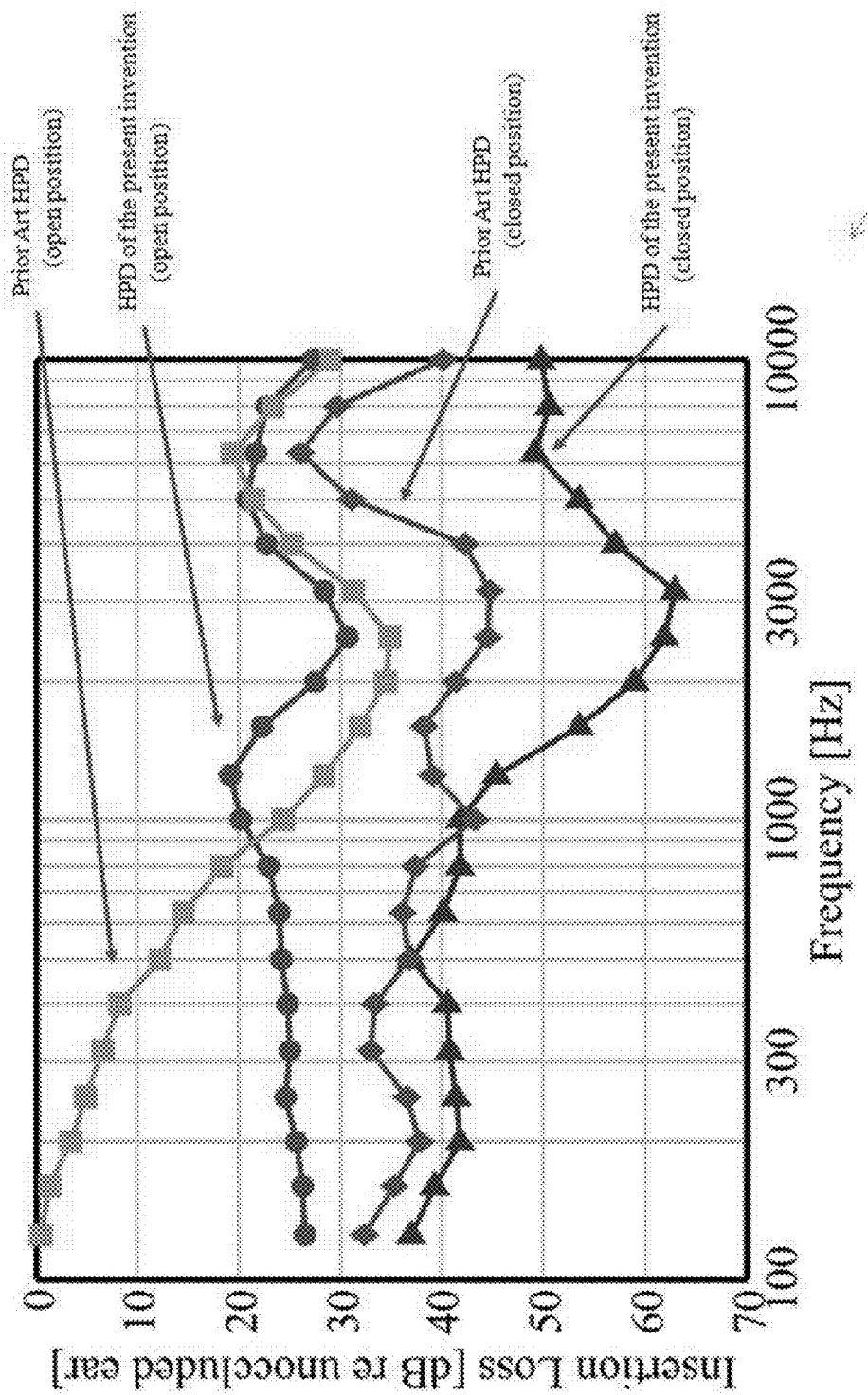
FIG. 4 is a graph showing insertion loss in dB over a range of frequencies for both the passive element of embodiments of the present invention, and a prior art passive hearing protection device, each as measured in an open and a closed position.

As shown in FIG. 1 the passive element 1 further comprises a tuning element 12 which flattens the frequency response of the sound waves passing through the element to prevent the typical low-pass filter effect of passive earplugs. The tuning element 12 may comprise a resonance chamber (or acoustic resonator cavity) 121 and/or one or more filter diaphragms 122. The chamber 121 and the diaphragms 122, each and in combination, achieve the flat-frequency response of the tuning element 12 by reducing the passage of low frequency sound (see FIG. 4). When multiple diaphragms 122 are used, they may be stacked one directly onto another in some embodiments, or separated by walls 110 in other embodiments.

Figure 3:
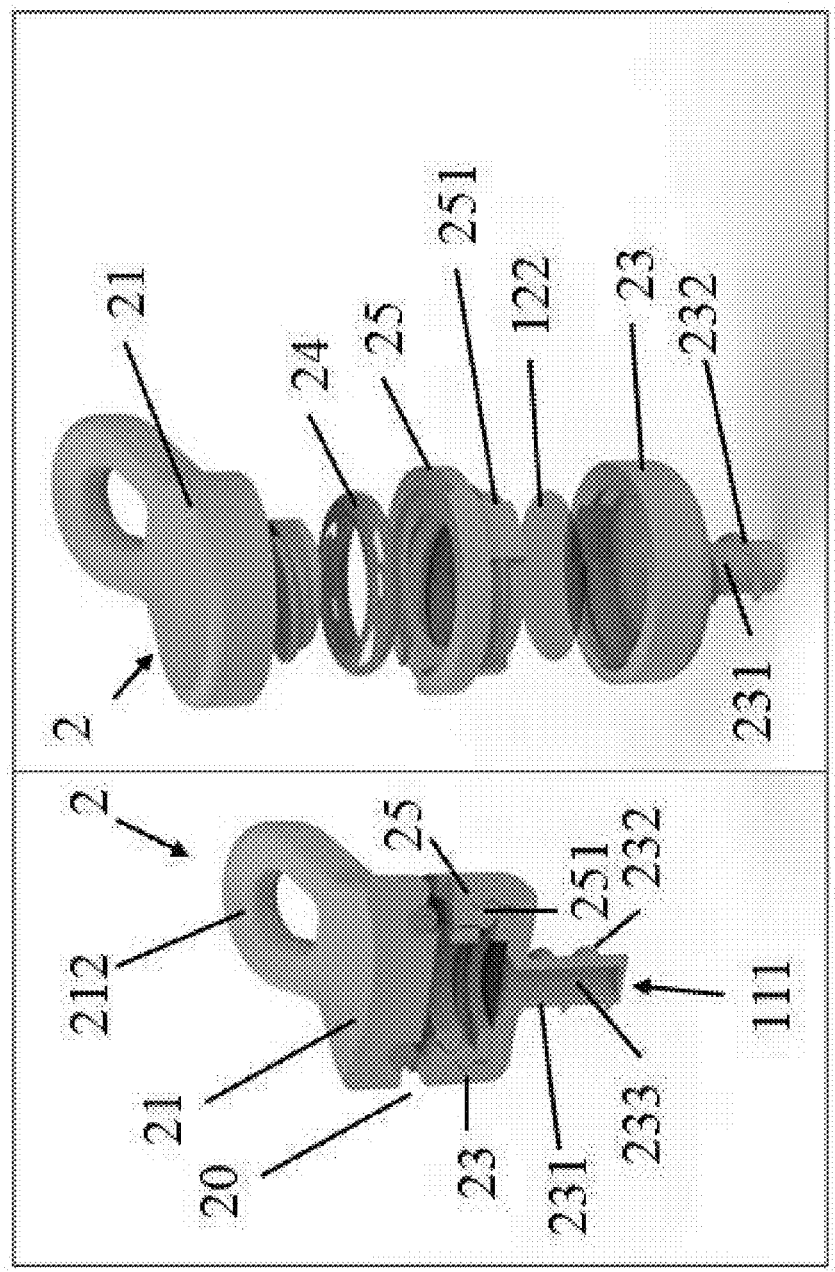
FIG. 3 shows a peripheral view of an embodiment of the present invention, assembled and unassembled.
Figure 8:
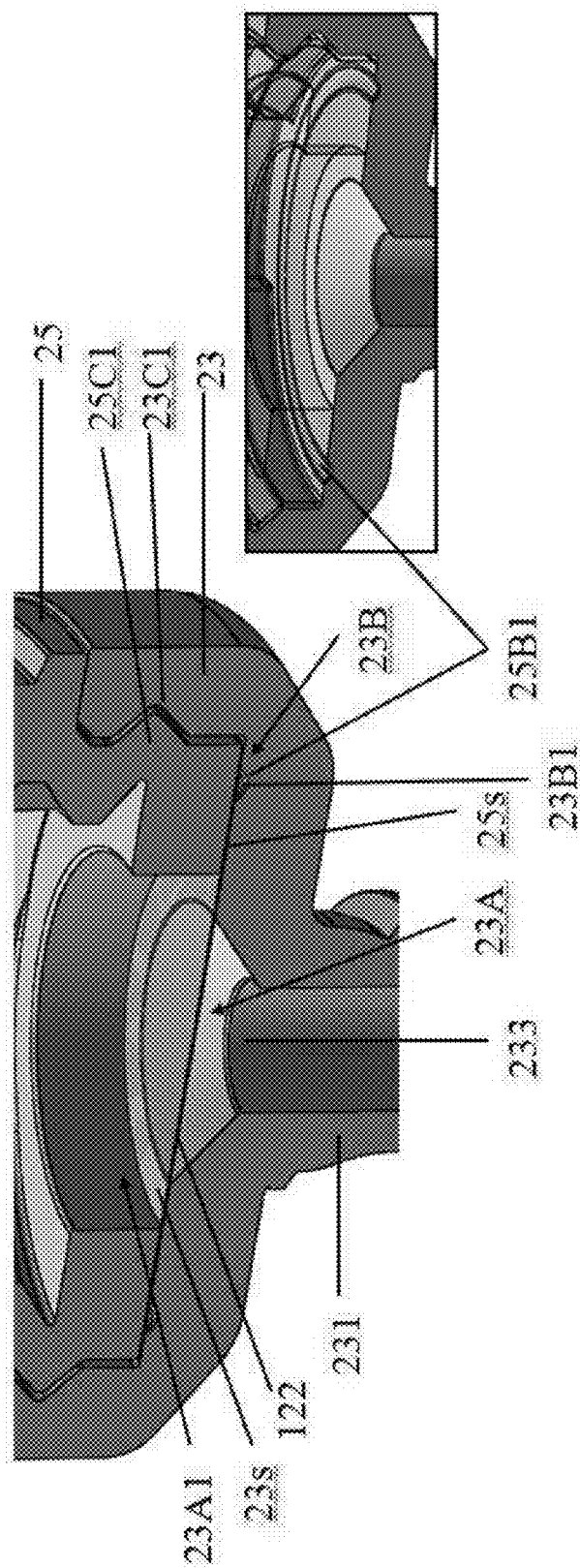
FIG. 8 shows an embodiment of the diaphragm clamping feature of an embodiment of the present invention, which creates uniform tension on the diaphragm.

Referring to FIGS. 3 and 8, in some embodiments the cavity 23A1 of resonator 121 is somewhat cylindrical, with an inner diameter of between 0.05' and 0.5", or 0.15" and 0.25", or about 0.2", and a height (in the open position) of between 0.02" and 0.2", or 0.165" and 0.185", or about 0.175". In some embodiments (shown in FIG. 8) a chamber consisting of conical cavity 23A atop a cylindrical cavity 233 is located below the diaphragm 122. The conical cavity 23A, in some embodiments has a major diameter between 0.02" and 0.2", or 0.125" and 0.175", or about 0.15", with a minor diameter between 0.02" and 0.2", or 0.05" and 0.10", or 0.07", and a height of between 0.01" and 0.1", or 0.03" and 0.05", or 0.04". In some embodiments, the cylindrical volume 233 (shaped for ease of manufacturing) has an inner diameter between 0.02" and 0.2", or 0.05" and 0.10", or 0.07", and a height of between 0.01' and 0.4", or 0.1" and 0.3", or 0.2".

The tuning element 12 may comprise a diaphragm 122, a resonator 121, or both, to achieve a flat frequency response. However, when a diaphragm 122 is present, cavities 23A and 23A1 must be integrated into the tuning element 12 on each side of the diaphragm to allow the diaphragm to flex and vibrate, and the cavities 23A and 23A1 function as resonators in such a configuration. The resonator 121 can provide such a cavity, on either side of the diaphragm 122. As shown in FIG. 8, the lower portion of a retainer ring 25 with the circumferential structure 251 extending therefrom and the diaphragm 122 can form the upper resonance chamber 23A1 of the passive element 1.

In some embodiments of the present invention the diaphragm 122 is manufactured from a biaxially-oriented polyethylene terephthalate (BoPET) material having a thickness of between 0.0003 and 0.003", or about 0.001", and a diameter of between about 0.1" to 0.5", or between 0.3" and 0.4", or about 0.345". The diaphragm 122 is supported by said housing structure 2 at its circumference.

The figures show the passive element 1 with the tuning element 12 supported in said housing structure 2 before the nonlinear acoustic filter 11 (12 is left of 11 in FIG. 1); however, in some embodiments of the present invention the tuning element 12 is supported after the nonlinear acoustic filter 11.

As shown in the embodiment of FIG. 3, the passive element comprising in series a nonlinear acoustic filter and a tuning element, is a component of the hearing protection device of the present invention, which is supported in a housing 2 comprising a cap 21, an ear-tip base 23, and a retainer ring 25. The nonlinear acoustic filter comprising a pinhole orifice 111 extends through the wall of said ear-tip base (for example), and the tuning element comprising a diaphragm 122 and resonance chambers formed in the ear tip base 23 and the retainer ring 25, above 23A1 and below 23A the diaphragm 122. In the embodiment shown, the ear-tip base 23 has a tubular structure 231 extending from the bottom thereof; in some embodiments this tubular structure 231 comprises structure 232 around its exterior to secure a foam ear tip 26 (shown in FIGS. 2, 5 and 7), and a hollow core (cylindrical cavity) 233, for secure placement within an external auditory meatus 9 (shown in FIG. 1). Foam ear tips suitable for use in the present invention include ear tips manufactured by Comply Inc. or other foam or silicone tips. The ergonomic cap or top 21 is manufactured with one or more apertures 20 (see, also, FIG. 7) to receive sound waves, and includes an extending portion 212 to allow a user to grip the unit and assist with insertion or removal of the same from the ear.

In some embodiments the base 23 comprises a diaphragm clamping feature 23B, which, when the diaphragm 122 is positioned within said feature (as shown in FIG. 8), creates uniform tension on the diaphragm. In the embodiment shown, the upper portion of the camping feature 23B extends from the circumferential structure 251 of the retainer ring 25 and comprises a circular ridge 25B1; the circular ridge 25B1 fits into a circular channel 23B1 of the ear-tip base 23. The diaphragm 122, when positioned between surfaces 25s and 23s, is thereby clamped in place by opposing surfaces with uniform tension provided by the mating of the circular ridge 25B1 and circular channel 23B1 of the ring 25 and the base 23. In some embodiments the retainer ring 25 is secured within the ear-tip base 23 by means of corresponding circumferential engagement structures 25C1 and 23C1 extending about the circumferential structure 251 of the retainer ring 25 and the interior upper lateral side of the ear-tip base 23.

Figure 7:
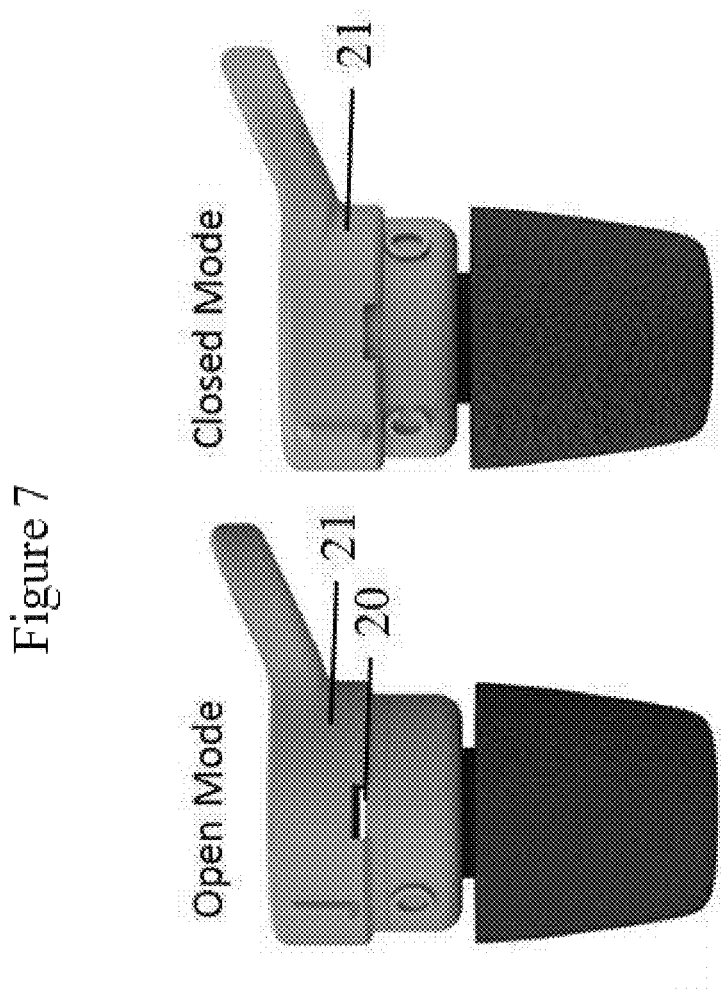
FIG. 7 shows an embodiment of the present invention, with the housing cap in the open and closed positions.

Integrating a plug or door to cover the entire sound inlet channel 20 in order to block any air path into the hearing protection device will offer supplementary protection in a loud continuous noise environment. One such embodiment is shown in FIG. 7 where the cap 21 of the housing 2 may also be designed to rotate between open and closed positions, so that by a turn of the cap 21 relative to the remainder of the housing 2, the sound inlet channel 20 can be opened (uncovered) or closed (covered). When the cap 21 is in the open position, the sound inlet channel 20 will allow clear transmission of sound, but at a reduced level, while also providing blast protection; when the cap 21 is in the closed position, the sound inlet channel 20 is closed off to give the maximum amount of protection against loud noise. In this embodiment, as shown in FIG. 3, an o-ring 24, which may be made from silicone or other suitable material, is compressed between the cap 21 and retaining ring 25 to further seal the sound inlet channel 20 in closed position.

Figure 2:
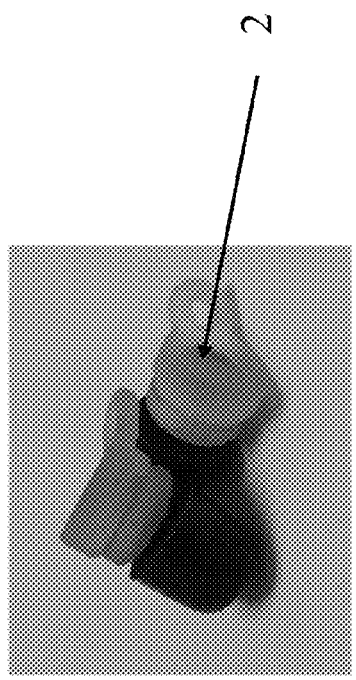
FIG. 2 is a picture of an embodiment of the present invention.
Figure 2A:
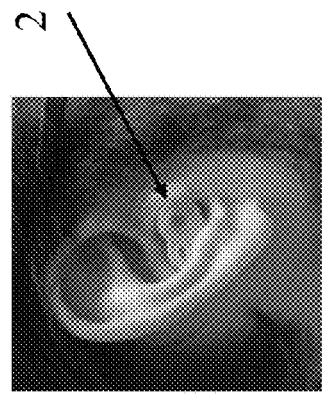
FIG. 2A is a picture of an embodiment of the present invention positioned in an ear.

The housing structure components, namely the cap 21, the retainer ring 25, and the base 23 of the embodiment of the device shown in FIGS. 3, 5, 7 and 8, have interlocking (shown as correspondingly threaded) circumferential structures to allow the components to form compactly as one housing structure 2. Preferably the components are made substantially from acrylonitrile butadiene styrene (ABS) plastic. Alternatively, the components may be fabricated from any solid material such as plastic or metal. An embodiment of the passive device in the housing 2 is shown in FIG. 2, and in an ear in FIG. 2A.

The passive element 1 of the device of the present invention creates a relatively flat response, whereby the insertion loss ranges from 18 to 30 dB in the frequency range of 100-10,000 Hz, as compared to a prior art passive model (3M Combat Arms Earplug) that has a vast range of insertion loss (from almost 0 dB at 100 Hz to 35 dB at 2500 Hz).

Figure 9:
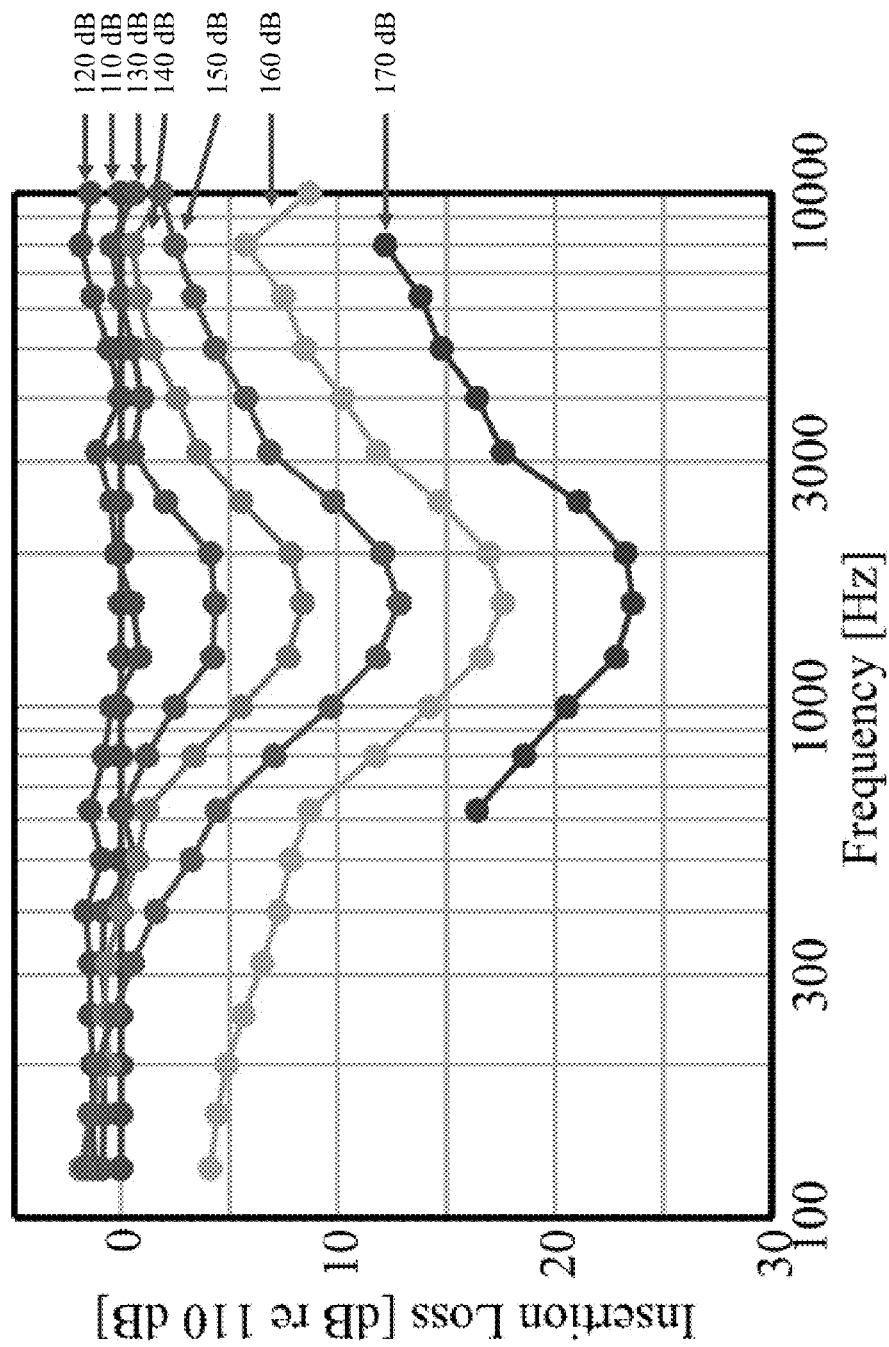
FIG. 9 shows the additional insertion loss provided by a passive hearing protector embodiment at various exposure levels in dB beyond the insertion loss provided at 110 dB (re 20 microPascals).

As shown in FIG. 9, when noise levels increase to 170 dB for example, the hybrid embodiment provides up to an additional 24 dB of insertion loss relative to the protection afforded at a 110 dB exposure level for a total of 55 dB of insertion loss. This capability to offer lower insertion loss at low noise levels and provide greater insertion loss at high noise levels (such as weapons fire) provides the user with the ability to maintain situational awareness and receive extra noise protection when needed.

Another embodiment of the present invention comprises a hybrid passive/electronic hearing protection device using the same passive element 1 for providing hearing protection as described above, but also having (as shown in FIG. 1) an active electronic element 3 to counteract the insertion loss provided by the passive element and restore natural hearing for low to moderate sound pressure levels. By inclusion of the active electronic element 3 of the present invention, sounds reduced by the passive nonlinear filter 11 may be amplified and sounds that fall below normal hearing levels when wearing hearing protection can be enhanced.

Figure 5:
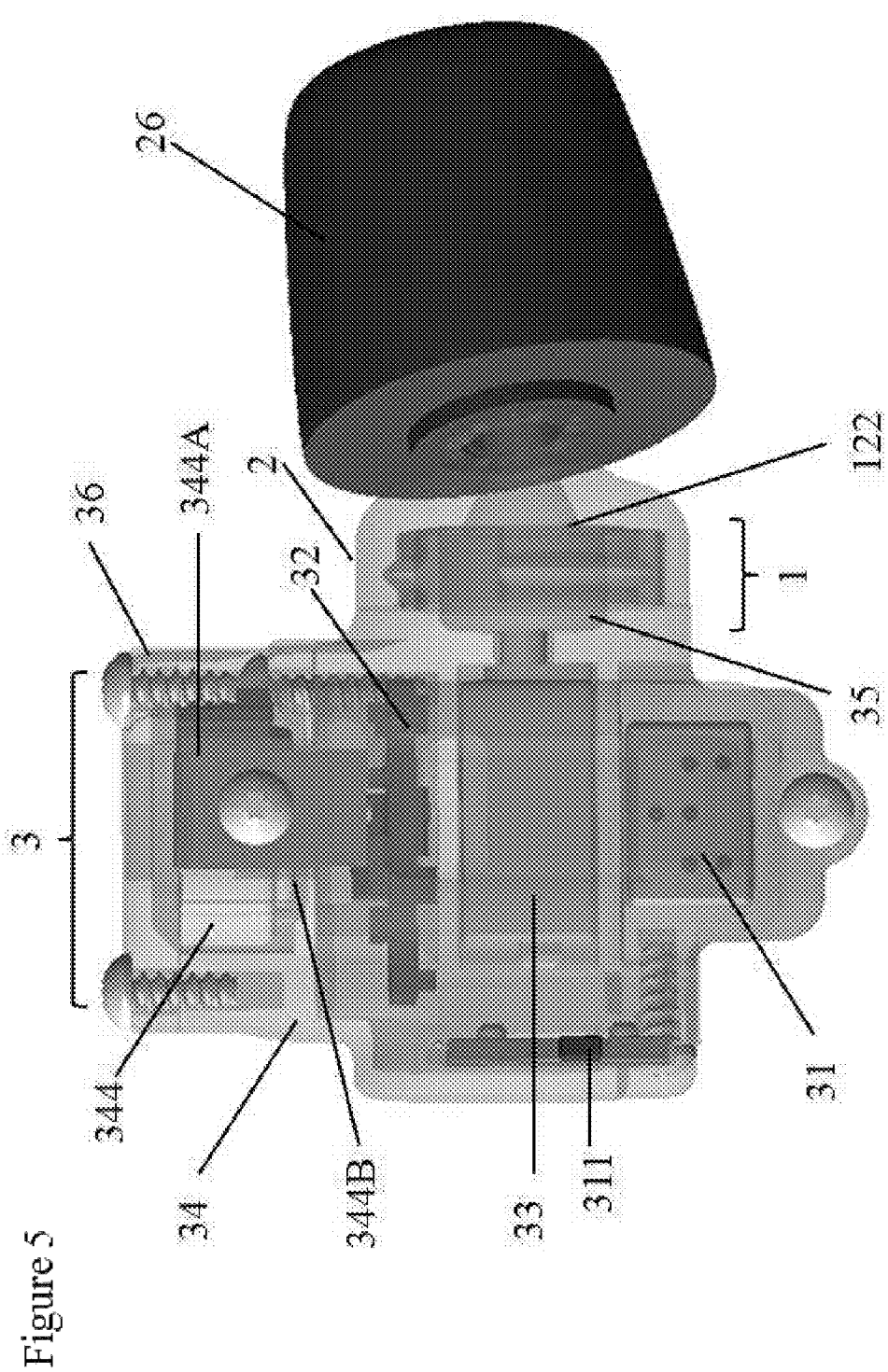
FIG. 5 is a schematic of a hybrid hearing protector embodiment of the present invention.
Figure 5B:
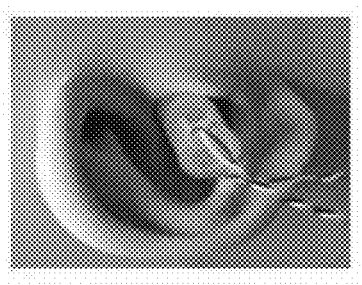
FIGS. 5A and 5B are pictures of different embodiments positioned in an ear.

As shown in FIGS. 1 and 5, the active electronic element 3 comprises an electronic microphone 31, a simple, inexpensive, low-power electronic amplifier circuit 32, and a speaker 33, to restore natural hearing. These electronic components are positioned in the hearing protection device either before or after the passive element 1 of the present invention. If the electronic element 3 is positioned before the passive element 1, sound passes through the electronic element 3 before passing through the passive element 1 and then into the external auditory meatus 9. If the electronic element 3 is positioned after the passive element 1, sound passes through the passive element 1 before passing through the electronic element 3 and then into the external auditory meatus 9. While the figures show the electronic element 3 before the passive element 1, the order can be reversed (FIG. 5B). When the passive element 1 is closest to the external auditory meatus, however, it acts to reduce the self-noise generated by the electronics and coming through the speaker 33 of the electronic element 3, resulting in a desirably low noise floor and allowing the user to better maintain awareness of the surrounding environment.

Figure 5A:
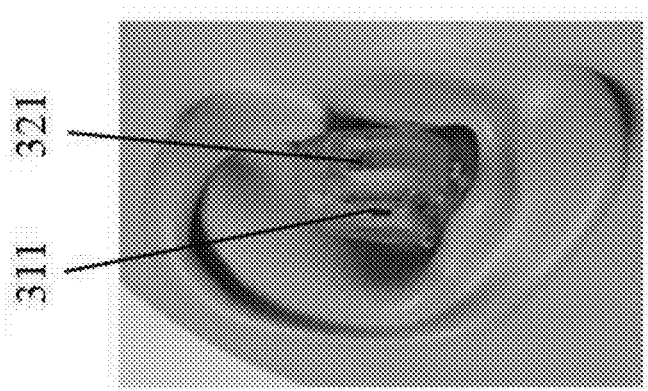

An embodiment of this hybrid hearing protection device of the present invention, as depicted in FIG. 5, has the passive element 1 positioned in the housing 2 after the electronic element 3. In this embodiment of the hybrid hearing protection device, the retainer ring 25 of the above mentioned embodiment of the passive device is replaced with a spacing ring 35 to clamp the diaphragm 122 in place and also define the volume (a substantially cylindrical volume with a diameter of about 0.2" and a length of about 0.12") of the cavity between the speaker 33 and the diaphragm 122 of the passive element 1. As shown in FIGS. 5 and 5A, electronic element 3 contains an electronics housing 34 having a microphone port 321, a high/low/off gain switch 311 for operating the amplifier circuit 32, and a cavity with a removable door 36 for receiving a battery 344 with battery terminals 344A and 344B. Like the housing structure hereinabove described for an embodiment of the passive device, the housing structure of this hybrid embodiment may include interlocking support structures.

Optionally, as shown in FIG. 1 a push-to-talk (PTT) feature can be incorporated within the hybrid hearing protection device (at 37), with a switch 38 to engage the PTT, and a radio system 39. This feature permits integration with communications (radio or phone) and entertainment devices using a standard audio jack or other communications system interface.

The hybrid hearing protection device achieves functionality equivalent to the expensive electronic hearing protection devices of the prior art, at a significantly reduced cost. The passive element 1 of the hybrid system continues to provide instant blast protection and noise compression at high sound pressure levels and yet achieves the natural flat frequency response, and the electronic element 3 restores natural hearing at low sound pressure levels. With optional inclusion of communications components, the hybrid system further provides situational awareness with the capability for radio integration.

Figure 6:
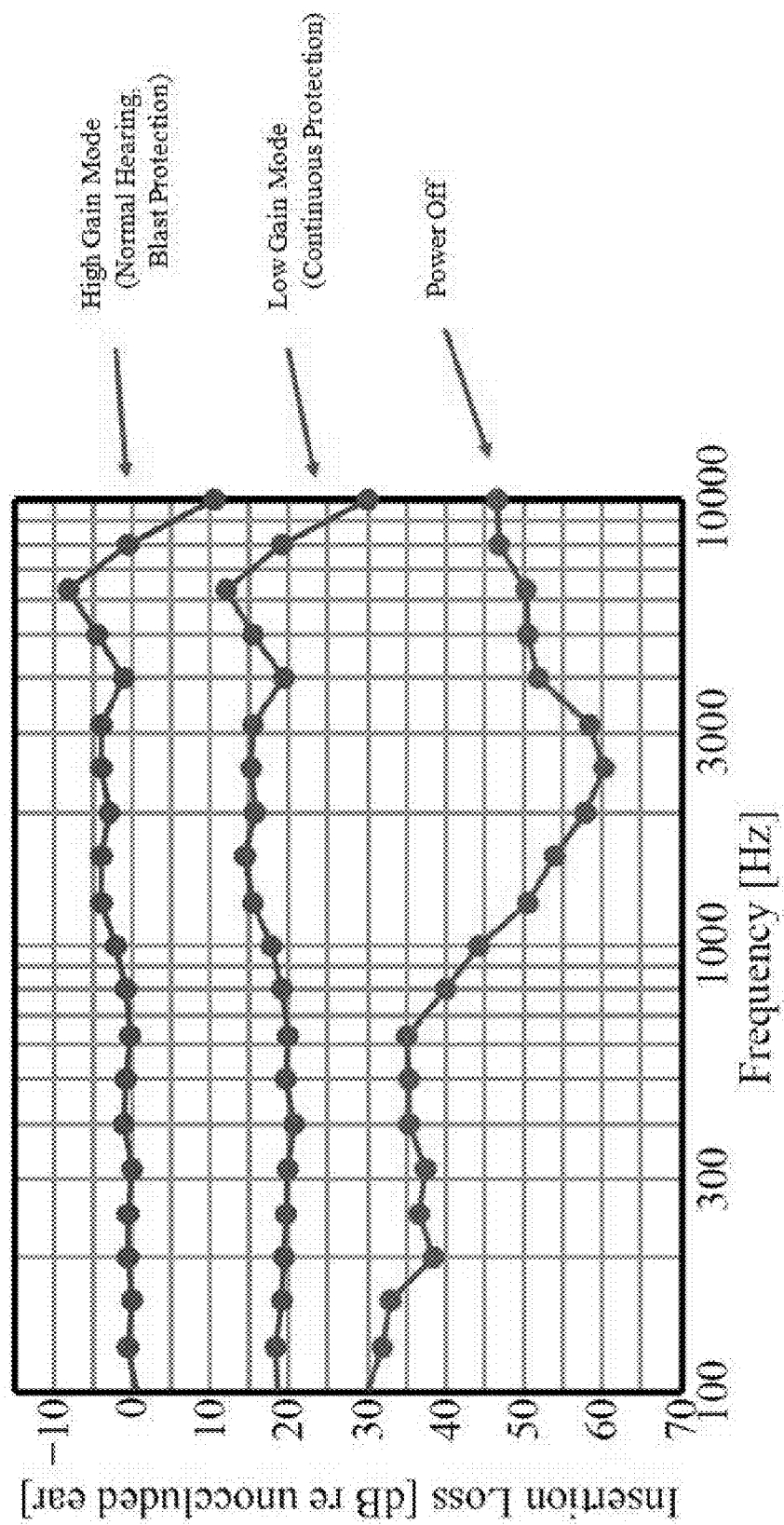
FIG. 6 is a graph showing insertion loss in dB over a range of frequencies of a hybrid hearing protector embodiment of the present invention. The top curve shows the frequency response in a high gain mode where approximately normal hearing is achieved. The middle curve shows the frequency response in a low gain mode where approximately 20 dB of insertion loss is provided over a range of frequencies. The bottom curve shows the frequency response when the device is powered off.

As shown in FIG. 6, when the power is off on the hybrid system of the present invention (i.e., the electronic components are not active), the insertion loss is more than 30 dB (lowest curve); the insertion loss decreases significantly when amplifying from a low gain mode (20 dB of insertion loss, middle curve) to a high gain mode (0 dB of insertion loss, upper curve). Furthermore, as shown in FIG. 6, the hybrid embodiment of the present invention has a relatively flat frequency response, and provides normal hearing (approximately 0 dB insertion loss as shown by upper curve) at low noise levels (e.g., 90 dB), when operated in a high gain mode. When operated in a low gain mode (FIG. 6, middle curve) the noise levels are reduced by about 24 dB from normal hearing as would be desirable in a louder environment.

Figure 10:
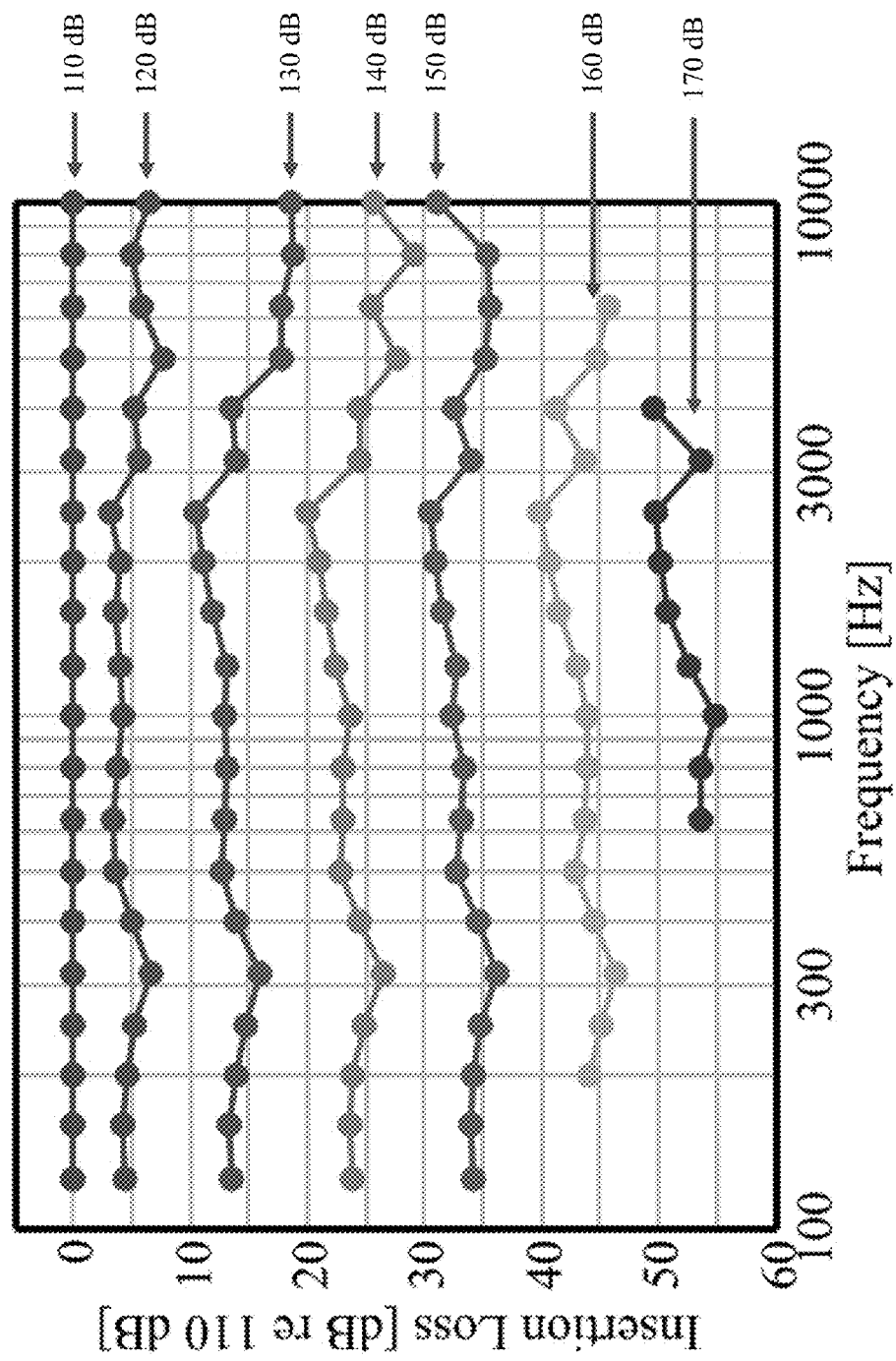
FIG. 10 shows the additional insertion loss provided by a hybrid hearing protector embodiment at various exposure levels in dB beyond the insertion loss provided at 110 dB (re 20 microPascals).

As shown in FIG. 10, when noise levels increase to 160 dB, for example, the hybrid embodiment provides an additional 45 dB of insertion loss beyond the protection afforded at a 110 dB exposure level for added protection. This capability to offer normal hearing at low noise levels, but attenuate sound at high noise levels (such as weapons fire) provides the user with the ability to maintain situational awareness and receive protection when needed (as sound levels increase).

The invention claimed is:

1. A hearing protection device intended to be inserted into an external auditory meatus of a user, the hearing protection device comprising:
   a passive tuning element;

an electronic element comprising an electronic microphone, a low power electronic amplifier circuit, and a speaker; and a housing structure having a first end and a second end, wherein the first end is intended to be inserted into said external auditory meatus of the user, the housing structure supporting the passive tuning element and the electronic element.

2. The hearing protection device of claim 1, wherein the electronic element is supported by the housing structure in series with the passive tuning element.

3. The hearing protection device of claim 1, wherein the passive tuning element comprises a resonance chamber and one or more diaphragms.

4. The hearing protection device of claim 3, wherein further comprising a passive nonlinear acoustic filter.

5. The hearing protection device of claim 4, wherein the passive nonlinear acoustic filter comprises one or more walls, each having one or more small, precision orifices.

6. The hearing protection device of claim 1, further comprising a passive nonlinear acoustic filter.

7. The hearing protection device of claim 6, wherein the passive nonlinear acoustic filter and the passive turning element are supported in series near the first end of the housing structure, and the electronic element is supported near the second end of the housing structure, to achieve low electronic self-noise and resulting low audible noise passing into the ear canal.

8. The hearing protection device of claim 6, wherein the passive nonlinear acoustic filter comprises one or more walls, each having one or more small, precision orifices.

9. The hearing protection device of claim 8, each wall of the passive nonlinear acoustic filter has a thickness of between 0.005" and 0.200".

10. The hearing protection device of claim 8, wherein each wall of the passive nonlinear acoustic filter is made substantially from acrylonitrile butadiene styrene (ABS) plastic.

11. The hearing protection device of claim 8, wherein the passive nonlinear acoustic filter comprises a plurality of walls, and wherein the walls are spaced apart by a distance of between about 0.001" and 0.200".

12. The hearing protection device of claim 11, wherein the orifices of the walls are aligned, and have a diameter of between 0.005" and 0.140".

13. The hearing protection device of claim 8, wherein the passive tuning element comprises a diaphragm, and wherein the housing structure supports the diaphragm about its circumference, and provides cavities on each face of said diaphragm.

14. The hearing protection device of claim 13, wherein the housing structure further comprises a retainer ring having a circumferential structure which, when positioned above and in contact about an area of the circumference of the diaphragm in the housing structure, forms one of the cavities.

15. The hearing protection device of claim 13, wherein the housing structure comprises a hollow, conical cavity positioned at a face of the diaphragm, the face directed towards the first end of the housing structure, and wherein the conical cavity has a major diameter at the face the diaphragm between 0.02" and 0.2", a minor diameter between 0.02" and 0.2", and a height of between 0.01" and 0.1".

16. The hearing protection device of claim 6, wherein the passive tuning element comprises a resonator.

17. A hearing protection device intended to be inserted into an external auditory meatus of a user, the hearing protection device comprising:

a nonlinear acoustic filter;

an electronic element comprising an electronic microphone, a low power electronic amplifier circuit, and a speaker; and a housing structure having a first end and a second end, wherein the first end is intended to be inserted into said external auditory meatus of the user, the housing structure supporting the nonlinear acoustic filter and the electronic element.

18. The hearing protection device of claim 17, wherein the nonlinear acoustic filter comprises a diaphragm supported by the housing structure about its circumference, and by its configuration provides cavities on each face of the diaphragm.

19. A hearing protection device intended to be inserted into an external auditory meatus of a user, the hearing protection device comprising:

a housing having a retainer ring and a base, each of the retainer ring and the base having cavities and circumferential walls with corresponding, interlocking structures, wherein the base further comprises a bottom surface with a pinhole orifice extending through the surface, a diaphragm supported about its circumference by the interlocking structures of the retainer ring and the base, the diaphragm separating the cavity of the retainer ring from the cavity of the base, and an electronic element comprising an electronic microphone, a low power electronic amplifier circuit, and a speaker.

20. The hearing protection device of claim 19, wherein the retainer ring comprises a circular ridge about its bottom surface, and the base comprises a corresponding circular channel about its top surface, sized and positioned to receive the circular ridge of the retainer ring and support the diaphragm about its circumference.

* * * * *